(12) United States Patent
Hansen et al.

(10) Patent No.: US 11,475,993 B1
(45) Date of Patent: Oct. 18, 2022

(54) METHOD OF UNLOCKING AN OPERATION OF A CLASS III MEDICAL DEVICE (71) Applicants: Scott Robert Hansen, Irvine, CA (US); Louisa Marie Hansen, Irvine, CA (US)

(72) Inventors: Scott Robert Hansen, Irvine, CA (US); Louisa Marie Hansen, Irvine, CA (US)

( * ) Notice: Subject to any disclaimer, the term of this patent is extended or adjusted under 35 U.S.C. 154(b) by 0 days.

(21) Appl. No.: 17/567,011

(22) Filed: Dec. 31, 2021

(51) Int. Cl.
G16H 40/40 (2018.01)
G16H 20/30 (2018.01)
G06K 7/10 (2006.01)
G16H 20/40 (2018.01)

(52) U.S. Cl.
CPC ......... *G16H 40/40* (2018.01); *G06K 7/10297* (2013.01); *G16H 20/30* (2018.01); *G16H 20/40* (2018.01)

(58) Field of Classification Search
None
See application file for complete search history.

(56) References Cited

U.S. PATENT DOCUMENTS

| | | | |
|---|---|---|---|
| 11,146,383 B1 | 10/2021 | Marquardt et al. | |
| 11,238,431 B2 | 2/2022 | Chen et al. | |
| 2005/0247319 A1* | 11/2005 | Berger | A61B 90/98 600/300 |
| 2006/0180647 A1 | 8/2006 | Hansen | |
| 2009/0091451 A1* | 4/2009 | Jones | G06K 7/0008 340/572.1 |
| 2010/0289627 A1* | 11/2010 | McAllister | H04L 9/3226 340/10.42 |
| 2010/0313413 A1* | 12/2010 | Sheats | H01L 25/0657 29/829 |
| 2010/0315205 A1* | 12/2010 | Egbert | G16H 10/40 235/492 |
| 2011/0112856 A1* | 5/2011 | Rousso | A61K 51/0491 705/2 |
| 2015/0324681 A1* | 11/2015 | Mats | G06K 19/07766 235/492 |
| 2019/0076100 A1* | 3/2019 | Narkiss | A61M 16/06 |

(Continued)

FOREIGN PATENT DOCUMENTS

| | | | | |
|---|---|---|---|---|
| DE | 102017220500 | | 5/2019 | |
| WO | WO-2010059376 A1 | * | 5/2010 | ............... A61N 1/05 |

OTHER PUBLICATIONS

Fei, Xiaolu, et al. "Application Safety Evaluation of the Radio Frequency Identification Tag Under Magnetic Resonance Imaging." Biomedical Engineering Online 13 (2014): n/a-129. ProQuest. Web. Sep. 7, 2022. (Year: 2014).*

(Continued)

*Primary Examiner* — Lena Najarian
(74) *Attorney, Agent, or Firm* — Scott R. Hansen; Viking IP Law (57) ABSTRACT A method of unlocking an operation of a Class III medical device suitable for use in treating, for example, COVID 19 in humans is presented. An integrated circuit is inserted or integrated into a medical device having an RFID reader, the medical device having a capability that is in a locked state. The integrated circuit has a first tiny RFID tag embedded therein. The RFID tag has an area of about 0.1 mm$^2$ or less. The RFID tag is a largely digital tag that is implemented using portable digital IP blocks, the RFID tag utilizing dual-phase RF-only logic.

16 Claims, 5 Drawing Sheets (56) References Cited

U.S. PATENT DOCUMENTS

2020/0042989 A1\* 2/2020 Ramadoss ............ G06Q 50/167
2021/0398667 A1\* 12/2021 Fujioka ................. G16H 50/20
2022/0027447 A1 1/2022 Keith, Jr.

OTHER PUBLICATIONS

"RFID and Blockchain Are Changing Supply Chains", Luke Hatkinson-Kent, RFID Journal, Apr. 11, 2018, https://www.rfidjournal.com/rfid-and-blockchain-are-changing-supply-chains (accessed Jan. 14, 2022).

"8 More Surprising Uses of RFID," by David Budiac, SoftwareConnect, Jan. 30, 2018, https://softwareconnect.com/rfid/8-more-surprising-uses-of-rfid/ (accessed Jan. 14, 2022).

"What Is RFID in Implantable Medical Devices?" Nursa.org, Jan. 10, 2022, https://www.nursa.org/what-is-rfid-in-implantable-medical-devices/, (accessed Jan. 14, 2022).

K. Bhanushali, et al. "A 125 μm×245 μm Mainly Digital UHF EPC Gen2 Compatible RFID Tag in 55 nm CMOS Process," in IEEE Journal of Radio Frequency Identification, vol. 5, No. 3, pp. 317-323, Sep. 2021, doi: 10.1109/JRFID.2021.3087448.

Zhao, Bo et al. "A Batteryless Padless Crystalless 116 μm×116 μm "Dielet" Near-Field Radio With On-Chip Coil Antenna." IEEE J. Solid State Circuits 55 (2020): 249-260.

\* cited by examiner

METHOD OF UNLOCKING AN OPERATION OF A CLASS III MEDICAL DEVICE

BACKGROUND

COVID 19 can be a devastating illness for those who are hospitalized for it. According to one study, COVID 19 symptoms in hospitalized patients included fever, fatigue, cough, and dyspnea. Among non-hospitalized patients, commonly reported symptoms included fatigue, fever, cough, and myalgia. The Further significant symptoms for hospitalized patients include vomiting, dyspnea, altered mental status, dehydration, and wheezing. Non-hospitalized patients also suffered rhinorrhea, headache, sore throat, and anosmia or ageusia. General symptoms and upper respiratory symptoms occurred earlier in disease, and anosmia, ageusia, lower respiratory symptoms, and gastrointestinal symptoms occurred later. (Vahey G M et al. Symptom Profiles and Progression in Hospitalized and Non-hospitalized Patients with Coronavirus Disease, Colorado, USA, 2020, EmergInfectDis.2021; 27(2):385-395.

COVID 19 can exacerbate other conditions. For example, one study indicates that 4 in 10 patients who contract COVID-19 on top of valvular heart disease (VHD) die within 30 days of hospital admission. That mortality rate, researchers say, is perhaps enough to justify pursuing valve repair or replacement even in the context of SARS-CoV-2. That is, because the mortality rate is so high, replacing a defective heart valve can be a critical procedure on a COVID 19 patient with valvular heart disease.

To treat these COVID 19 effects, hospitals must often use a variety of medical equipment, including Class III medical device as defined by the FDA, and that are suitable for use in treating COVID 19 and/or related health issues in a human body and that require regulatory premarket approval to evaluate the safety and effectiveness of the device. Generally, Class III medical devices have a high risk to patients or users. These devices help sustain or support life, can be implanted, and/or present potential unreasonable risk of illness or injury. They represent about 10% of medical devices. A few of many examples are defibrillators, pacemakers, various implants, including implanted prosthetics. Many Class III medical devices incorporate integrated circuits (ICs).

A challenge has been verifying that an IC and/or a component of which the IC is a component is genuine, suitable for use in a Class III medical device, or a counterfeit. Counterfeit integrated circuits have been a widespread problem in technology, generally. An IC that is counterfeit may not meet the rigorous demands on it that a Class III medical device can require, potentially posing a risk to patients and/or treatment providers. This is especially true in the challenging setting of treating COVID 19 patients.

Another challenge is that traditional Radio Frequency ID (RFID) tags require significant surface area and can present issues when incorporated into medical devices, especially small medical devices that are implanted into a human body, as well as in other medical devices.

Embodiments of the present disclosure may include a method of unlocking an operation of a Class III medical device suitable for use in treating COVID 19 in humans, the method including the steps of inserting an integrated circuit into a medical device having an RFID reader, the medical device having a capability that may be in a locked state, the integrated circuit having a first tiny RFID tag embedded therein, the RFID tag having an area of about 0.1 mm2 or less and being largely digital utilizing RF-only logic.

BRIEF SUMMARY

Embodiments of the present disclosure may include a method of unlocking an operation of a Class III medical device suitable for use in treating COVID 19 in humans, the method including the steps of inserting an integrated circuit into a medical device having an RFID reader, the medical device having a capability that may be in a locked state, the integrated circuit having a first tiny RFID tag embedded therein, the RFID tag having an area of about 0.1 mm2 or less and being largely digital utilizing RF-only logic.

Embodiments may also include reading data from the first RFID tag. Embodiments may also include verifying that the RFID data that has been read from the first RFID tag meets criteria for unlocking the device. Embodiments may also include after verifying the RFID data from the first RFID tag, unlocking the capability of the device for operation. In some embodiments, the integrated circuit further may include a second embedded tiny RFID tag that may be spaced apart from the first RFID tag, the second RFID tag having an area of about 0.1 mm2 or less. the method further including reading data from the second RFID tag. In some embodiments, the device may be a Class III medical device as defined by the FDA, and may be suitable for use in treating COVID 19 in a human body and requires regulatory premarket approval to evaluate the safety and effectiveness of the device.

Embodiments of the present disclosure may also include a method of unlocking an operation of a Class III medical device suitable for use in treating COVID 19 in humans, the method including the steps of inserting an integrated circuit into a medical device having an RFID reader, the medical device having a capability that may be in a locked state. In some embodiments, the integrated circuit having a first tiny RFID tag embedded therein, the RFID tag having an area of 0.1 mm2 or less, the RFID tag being a largely digital tag that may be implemented using portable digital IP blocks, the RFID tag utilizing dual-phase RF-only logic.

Embodiments may also include power supply transistors may be shared across an integrated circuit chip and a foundry standard cell library may be used in manufacturing the tiny RFID tag. Embodiments may also include reading data from the tiny RFID tag. Embodiments may also include verifying that the RFID data that has been read meets criteria for unlocking the device. Embodiments may also include after verifying the RFID data, unlocking the capability of the device for operation. In some embodiments, the device may be a Class III medical device as defined by the FDA, and may be suitable for use in treating COVID 19 in a human body and requires regulatory premarket approval to evaluate the safety and effectiveness of the device.

In some embodiments, the medical device may be an oxygen delivery device, the method further including delivering oxygen to the body. In some embodiments, the medical device delivers nanoparticles into a human body, the method further including delivering nanoparticles into the body. In some embodiments, the medical device assists function of a human kidney, the method further including assisting the function of a human kidney.

In some embodiments, the medical device may be adapted to be implanted in a human body, the method further including implanting at least a component of the medical device into the human body. In some embodiments, the medical device may be a cardiac device, the method further including assisting cardiac function in a human with the cardiac device. In some embodiments, the medical device may be an implantable prosthesis, the method further including the step of implanting the implantable prosthesis into a human.

In some embodiments, the medical device may be an internet of things (TOT) device, the method further including connecting the device to a computer network. In some embodiments, the RFID data includes data sufficient to identify a uniform resource locator (URL). In some embodiments, the RFID data may be encoded solely at a foundry and may be not user-programmable. In some embodiments, the method further including encoding the RFID tag with data at a foundry.

In some embodiments, the step of unlocking the device further includes enabling a blockchain transaction. In some embodiments, the step of unlocking the device further includes enabling a cryptocurrency transaction. In some embodiments, the cryptocurrency transaction may be to pay for a medical procedure. Embodiments may also include one of the integrated circuit and the device has a non-fungible token (NFT) associated with it.

In some embodiments, the RFID data includes an identifier correlating the non-fungible token (NFT) with the integrated circuit or device. In some embodiments, the integrated circuit may be on a card, the method further including inserting the card into the device. In some embodiments, the device includes an RFID reader and at least a second component that may be not an RFID reader, the RFID reader and the second component being digitally interconnected but physically spaced apart.

In some embodiments, the medical device employs artificial intelligence (AI) and/or machine learning, the step of unlocking a capability of the device may include unlocking an artificial intelligence and/or machine learning capability. In some embodiments, the medical device has a machine vision capability, the step of unlocking a capability of the device may include unlocking a machine vision capability.

In some embodiments, the RFID tag has a sensitivity of −2 dBm or better. In some embodiments, the RFID tag operates in the 860-960 MHz band. In some embodiments, the RFID reader uses an ASK modulation scheme. In some embodiments, circuit operation may be paused during low-RF periods. In some embodiments, the integrated circuit may be part of at least one of a hard disk drive (HDD), a solid state drive (SSD), and flash memory card.

In some embodiments, the integrated circuit may be part of a biometric authentication device. In some embodiments, the method, further including the step of interacting between the medical device and the integrated circuit after the RFID data may be verified. In some embodiments, the integrated circuit may include a second RFID tag, the method further including reading data from the second RFID tag.

In some embodiments, the second RFID tag may be imbedded in the integrated circuit, has an area of 0.1 mm$^2$ or less, and may be spaced apart from the first RFID tag. In some embodiments, the method further may include the step of verifying data from both the first and the second RFID tag to unlock the device. In some embodiments, the integrated circuit may be part of a component, and the method further may include the step of the component interrogating the medical device, receiving a reply from the medical device, and providing the medical device access to an aspect of the component when the reply may be acceptable. In some embodiments, the step of unlocking may include enabling transmission of at least one of video and audio. In some embodiments, the embedded RFID tag may be part of a hospital patient bracelet. In some embodiments, the hospital patient bracelet includes writable memory, the method further including the step of reading data from the memory and writing new data to the memory.

Embodiments of the present disclosure may also include a method of unlocking an operation of a medical device, the method including the steps of inserting an integrated circuit into a medical device having an RFID reader, the medical device having a capability that may be in a locked state, the integrated circuit having a first tiny RFID tag embedded therein, the embedded RFID tag having an area of 0.1 mm$^2$ or less. Embodiments may also include reading data from the tiny RFID tag. Embodiments may also include verifying that the RFID data that has been read meets criteria for unlocking the device. Embodiments may also include after verifying the RFID data, unlocking the capability of the device for operation. In some embodiments, the medical further may include implanting the device into an animal in a veterinary setting. In some embodiments, the step of implanting the device into an animal in a veterinary setting may include transvenous pacemaker implantation. In some embodiments, the step of implanting the device into an animal in a veterinary setting may include implanting a prosthetic device.

A further embodiment relates to a method of unlocking an operation of a medical device that has a locked mode in which a capability of the medical device is locked and an unlocked mode in which a capability of the medical device is unlocked. The method includes; reading data from a tiny, largely-digital RFID tag that is embedded in an integrated circuit (IC) chip, the RFID tag having an area of about 0.1 mm$^2$ or less and occupying less than 10% of the area of the chip, and wherein power supply transistors are shared across the integrated circuit chip; Verifying that the RFID data that has been read meets criteria for unlocking a capability of the device; and after the step of verifying the RFID data meets criteria for unlocking a capability of the device, unlocking the capability of the medical device for operation.

Additional and/or alternative features that may be incorporated into any of the foregoing embodiments may include that the medical device is used in a veterinary setting on non-human animals. In one specific embodiment, the medical device is a transcutaneous electrical nerve stimulator and the method includes the step of performing transcutaneous electrical nerve stimulation. In another embodiment, the medical device is a pulse electromagnetic field (PEMF) therapy device, and the method includes the step of performing PEMF therapy. In another embodiment, the medical device has a laser, and the method includes performing veterinary laser therapy.

In any of the foregoing embodiments, various additional steps and/or other details may be incorporated, either separately or in combination with one or more other features. Consequently, the invention is not limited to specific combinations of elements, and may be comprised of a combination of steps and/or features not specifically identified herein.

DETAILED DESCRIPTION

Figure 1:
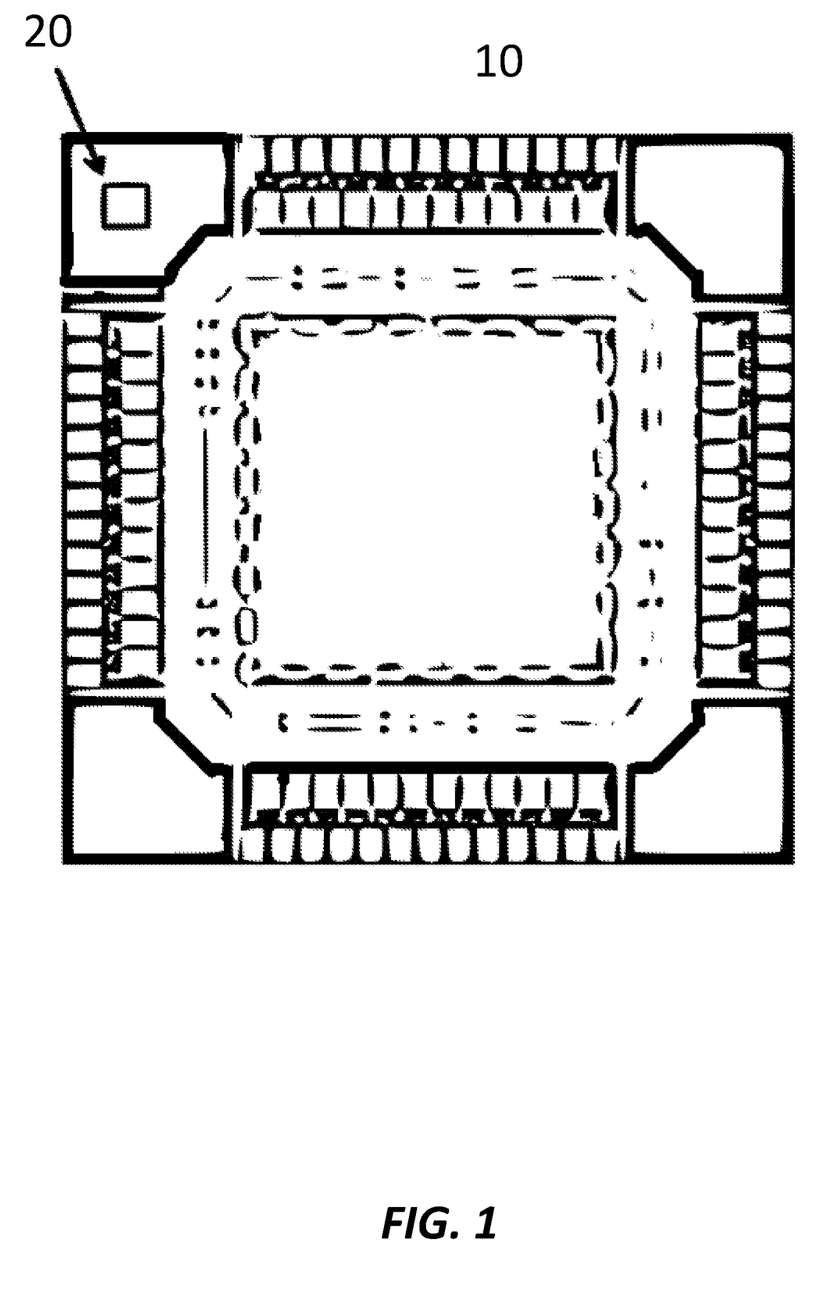
FIG. 1 is an integrated circuit chip with an RFID tag embedded in it.

FIG. 1 illustrates an integrated circuit chip 10 having an embedded RFID tag 20, the integrated circuit having a first tiny RFID tag embedded therein, the RFID tag having an area of 0.1 mm2 or less, the RFID tag being a largely digital tag that may be implemented using portable digital IP blocks, the RFID tag utilizing dual-phase RF-only logic. Power supply transistors may be shared across the integrated circuit chip and a foundry standard cell library may be used in manufacturing the tiny RFID tag. The RFID tag may optionally be encoded with data at the foundry at which it is made, and only optionally have user-programmable capacity.

Figure 2:
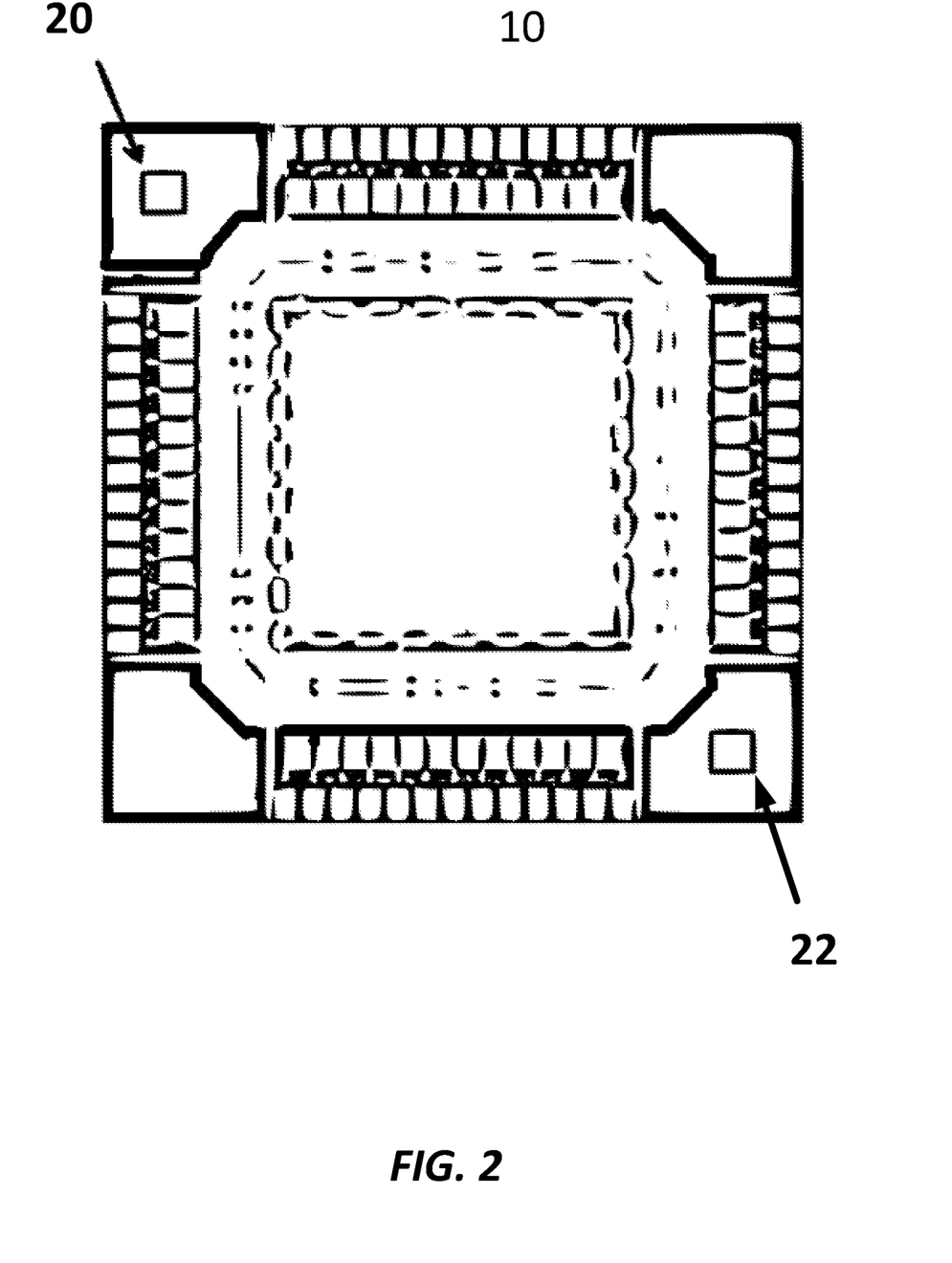
FIG. 2 is an integrated circuit chip with two RFID tags embedded in it.

FIG. 2 illustrates an integrated circuit chip 10 having a first embedded RFID tag 20, and a second embedded RFID tag 22. Consequently, FIG. 2 illustrates that in one embodiment, more than one RFID tag may be embedded in the integrated circuit chip. As a further possibility, more than two RFID tags may be embedded in the integrated circuit chip. Also, it is possible to use a second RFID tag in a system according to the present invention, in which the second RFID tag is embedded into a second integrated circuit chip, or is simply an RFID tag not embedded in chip.

Figure 3:
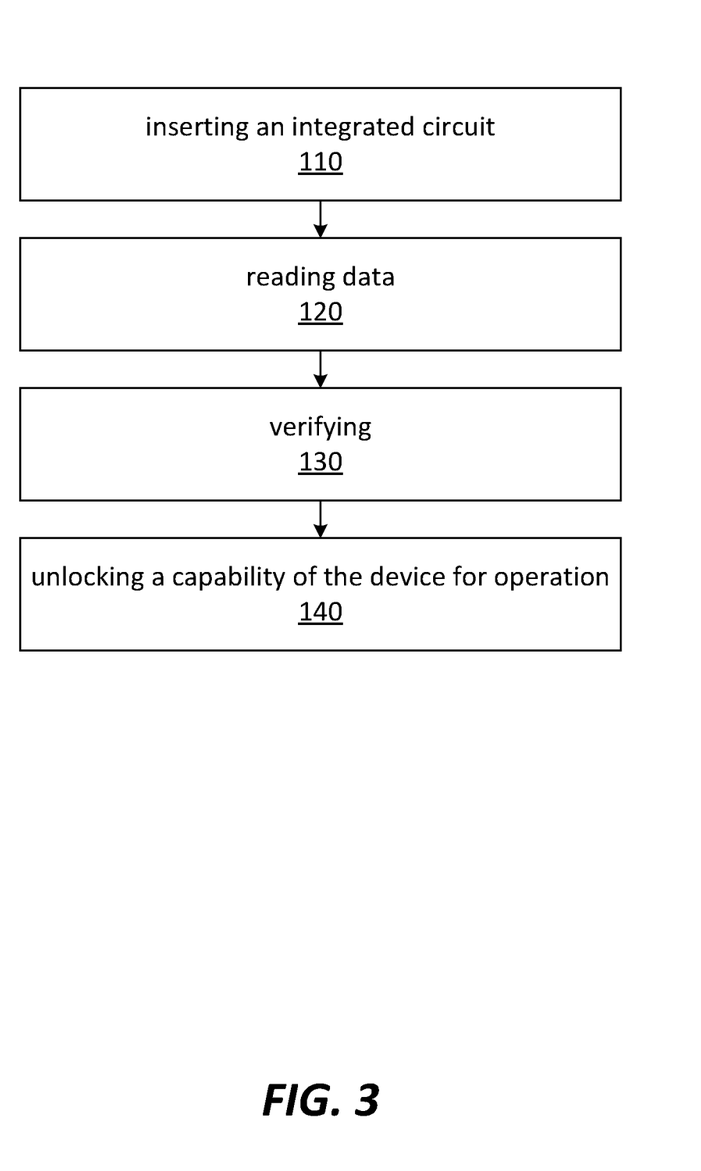
FIG. 3 is a flowchart illustrating a method of unlocking an operation of a Class III medical device, according to some embodiments of the present disclosure.
Figure 4:
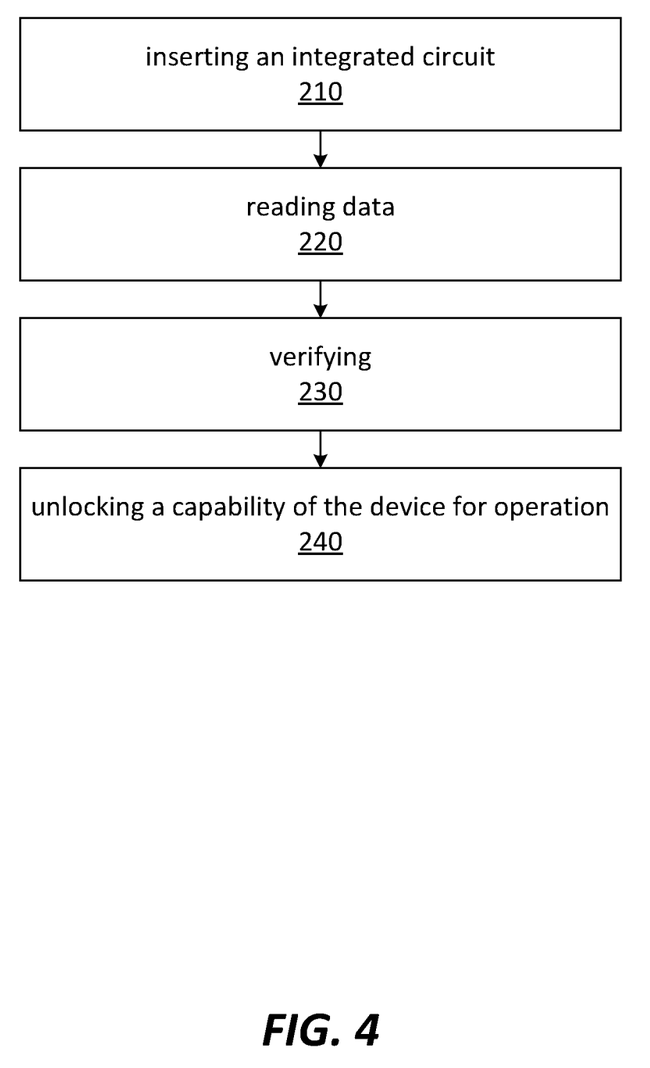
FIG. 4 is a flowchart illustrating a method of unlocking an operation of a Class III medical device, according to some embodiments of the present disclosure.
Figure 5:
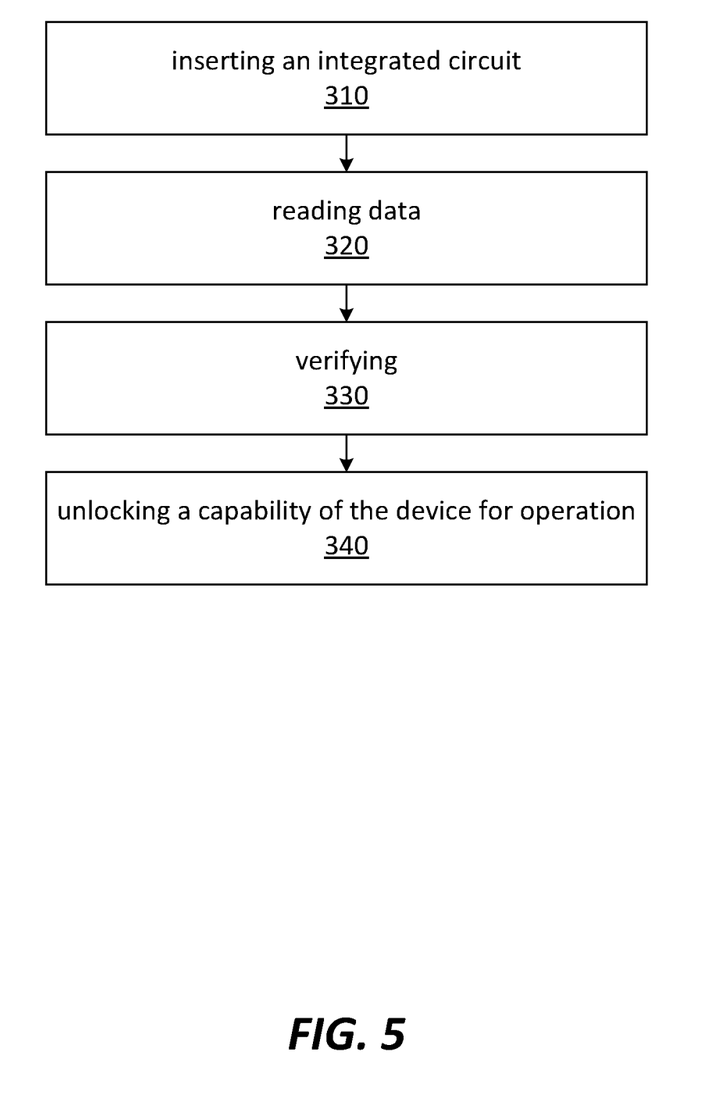
FIG. 5 is a flowchart illustrating a method of unlocking an operation of a medical device, according to some embodiments of the present disclosure.

FIG. 3 is a flowchart that shows a method of unlocking an operation of a Class III medical device, according to some embodiments of the present disclosure. At 110, the method may include inserting an integrated circuit into a medical device having an RFID reader, the medical device having a capability that may be in a locked state, the integrated circuit having a first tiny RFID tag embedded therein, the RFID tag having an area of about 0.1 mm2 or less and being largely digital utilizing RF-only logic. At 120, the method may include reading data from the first RFID tag.

At 130, the method may include verifying that the RFID data that has been read from the first RFID tag meets criteria for unlocking the device. At 140, the method may include, after verifying the RFID data from the first RFID tag, unlocking the capability of the device for operation. In some embodiments, the integrated circuit may further comprise a second embedded tiny RFID tag that may be spaced apart from the first RFID tag, the second RFID tag having an area of about 0.1 mm2 or less. the method further comprising reading data from the second RFID tag. In some embodiments, the device may be a Class III medical device as defined by the FDA, and may be suitable for use in treating COVID 19 in a human body and requires regulatory premarket approval to evaluate the safety and effectiveness of the device.

FIG. 2 is a flowchart that shows a method of unlocking an operation of a Class III medical device, according to some embodiments of the present disclosure. At 210, the method may include inserting an integrated circuit into a medical device having an RFID reader, the medical device having a capability that may be in a locked state. In some embodiments, the integrated circuit having a first tiny RFID tag embedded therein, the RFID tag having an area of 0.1 mm2 or less, the RFID tag being a largely digital tag that may be implemented using portable digital IP blocks, the RFID tag utilizing dual-phase RF-only logic.

In some embodiments, power supply transistors may be shared across an integrated circuit chip and a foundry standard cell library may be used in manufacturing the tiny RFID tag. At 220, the method may include reading data from the tiny RFID tag. At 230, the method may include verifying that the RFID data that has been read meets criteria for unlocking the device. At 240, the method may include, after verifying the RFID data, unlocking the capability of the device for operation.

In some embodiments, the device may be a Class III medical device as defined by the FDA, and may be suitable for use in treating COVID 19 in a human body and requires regulatory premarket approval to evaluate the safety and effectiveness of the device. In some embodiments, the medical device may be an oxygen delivery device, the method further comprising delivering oxygen to the body. In some embodiments, the medical device may deliver nanoparticles into a human body, the method further comprising delivering nanoparticles into the body.

In some embodiments, the medical device may assist function of a human kidney, the method further comprising assisting the function of a human kidney. In some embodiments, the medical device may be adapted to be implanted in a human body, the method further comprising implanting at least a component of the medical device into the human body. In some embodiments, the medical device may be a cardiac device, the method further comprising assisting cardiac function in a human with the cardiac device.

In some embodiments, the medical device may be an implantable prosthesis, the method further comprising the step of implanting the implantable prosthesis into a human. In some embodiments, the medical device may be an internet of things (TOT) device, the method further comprising connecting the device to a computer network. In some embodiments, the RFID data may include data sufficient to identify a uniform resource locator (URL).

In some embodiments, the RFID data may be encoded solely at a foundry and may be not user-programmable. In some embodiments, the method further comprising encoding the RFID tag with data at a foundry. In some embodiments, the step of unlocking the device may further include enabling a blockchain transaction. In some embodiments, the step of unlocking the device may further include enabling a cryptocurrency transaction.

In some embodiments, the cryptocurrency transaction may be to pay for a medical procedure. In some embodiments, one of the integrated circuit and the device may have a non-fungible token (NFT) associated with it. In some embodiments, the RFID data may include an identifier correlating the non-fungible token (NFT) with the integrated circuit or device. In some embodiments, the integrated circuit may be on a card, the method further comprising inserting the card into the device.

In some embodiments, the device may include an RFID reader and at least a second component that may be not an RFID reader, the RFID reader and the second component being digitally interconnected but physically spaced apart. In some embodiments, the medical device may employ artificial intelligence (AI) and/or machine learning, the step of unlocking a capability of the device comprises unlocking an artificial intelligence and/or machine learning capability.

In some embodiments, the medical device may have a machine vision capability, the step of unlocking a capability of the device comprises unlocking a machine vision capability. In some embodiments, the RFID tag may have a sensitivity of −2 dBm or better. In some embodiments, the RFID tag may operate in the 860-960 MHz band. In some embodiments, the RFID reader may use an ASK modulation scheme. In some embodiments, circuit operation may be paused during low-RF periods.

In some embodiments, the integrated circuit may be part of at least one of a hard disk drive (HDD), a solid state drive (SSD), and flash memory card. In some embodiments, the integrated circuit may be part of a biometric authentication device. In some embodiments, the step of interacting between the medical device and the integrated circuit after the RFID data may be verified. In some embodiments, the integrated circuit may comprise a second RFID tag, the method further comprising reading data from the second RFID tag.

In some embodiments, the second RFID tag may be imbedded in the integrated circuit, has an area of 0.1 mm2 or less, and may be spaced apart from the first RFID tag. In some embodiments, the method further comprises the step of verifying data from both the first and the second RFID tag to unlock the device. In some embodiments, the integrated circuit may be part of a component, and the method further comprises the step of the component interrogating the medical device, receiving a reply from the medical device, and providing the medical device access to an aspect of the component when the reply may be acceptable. In some embodiments, the step of unlocking comprises enabling transmission of at least one of video and audio. In some embodiments, the embedded RFID tag may be part of a hospital patient bracelet. In some embodiments, the hospital patient bracelet may include writable memory, the method further comprising the step of reading data from the memory and writing new data to the memory.

FIG. 3 is a flowchart that shows a method of unlocking an operation of a medical device, according to some embodiments of the present disclosure. At 310, the method may include inserting an integrated circuit into a medical device having an RFID reader, the medical device having a capability that may be in a locked state, the integrated circuit having a first tiny RFID tag embedded therein, the embedded RFID tag having an area of 0.1 mm2 or less. At 320, the method may include reading data from the tiny RFID tag. At 330, the method may include verifying that the RFID data that has been read meets criteria for unlocking the device.

At 340, the method may include, after verifying the RFID data, unlocking the capability of the device for operation. In some embodiments, the medical further comprises implanting the device into an animal in a veterinary setting. In some embodiments, the step of implanting the device into an animal in a veterinary setting comprises transvenous pacemaker implantation. In some embodiments, the step of implanting the device into an animal in a veterinary setting comprises implanting a prosthetic device.

Concerning the locking/unlocking function, one approach is a software-controlled system, in which the software maintains the system in a locked configuration unless a condition is satisfied. For example, the software only unlocks a capability of the device when data read from the RFID tag satisfies a criteria. Alternatively, electro-mechanical and/or mechanical locking systems may be employed.

It is assumed in the foregoing that various optional features are, standing alone and in isolation from the claimed combination of elements, known in the art. For example, it is known in the art how blockchain transactions are done, how cryptocurrency can be used to purchase goods or services, and the like.

Various optional and/or additional aspects may be incorporated into embodiments of the invention, and other variations are possible. Consequently, the foregoing is presented by way of example and not limitation:

What is claimed is:

1. A method of unlocking an operation of a Class III medical device suitable for use in treating COVID 19 in humans, the method comprising the steps of:
   inserting an integrated circuit into a medical device having a Radio Frequency Identification (RFID) reader, the medical device having a capability that is in a locked state;
   the integrated circuit having a first tiny RFID tag embedded therein, the first tiny RFID tag having an area of about 0.1 mm$^2$ or less, the first tiny RFID tag being a primarily digital tiny tag that is implemented using portable digital IP blocks, the first tiny RFID tag utilizing dual-phase RF-only logic;
   wherein power supply transistors are shared across an integrated circuit chip and a foundry standard cell library is used in manufacturing the first tiny RFID tag;
   reading data from the first tiny RFID tag;
   verifying that the RFID data that has been read meets criteria for unlocking the medical device; and
   after verifying the RFID data, unlocking the capability of the medical device for operation;
   wherein the medical device is a Class III medical device as defined by the Food and Drug Administration (FDA), and is suitable for use in treating COVID 19 in a human body and requires regulatory premarket approval to evaluate the safety and effectiveness of the medical device, and is an internet-of-things (IOT) cardiac device that is implantable in the human body; and
   the method further comprising implanting at least a component of the medical device into the human body;
   the method further comprising assisting cardiac function in the human body with the cardiac device;
   the method further comprising connecting the medical device to a computer network;
   the RFID data is encoded solely at a foundry and is not user-programmable, wherein the method further comprising encoding the first tiny RFID tag with data at the foundry;
   the method further comprises the step of interacting between the medical device and the integrated circuit after the RFID data is verified; and
   the method further comprises the step of the component interrogating the medical device, receiving a reply from the medical device, and providing the medical device access to an aspect of the component when the reply is acceptable.

2. The method of claim 1, in which the integrated circuit is on a card, the method further comprising inserting the card into the medical device.

3. The method of claim 1, in which the medical device includes the RFID reader and at least a second component that is not an RFID reader, the RFID reader and the second component being digitally interconnected but physically spaced apart.

4. The method of claim 1, in which the medical device employs artificial intelligence (AI) and/or machine learning, the step of unlocking the capability of the medical device comprises unlocking an artificial intelligence and/or machine learning capability.

5. The method of claim 1, wherein the RFID tag has a sensitivity of −2 dBm or better.

6. The method of claim 1, wherein the RFID tag operates in the 860-960 MHz band.

7. The method of claim 1, wherein the RFID reader uses an ASK modulation scheme in which circuit operation is paused during low-RF periods.

8. The method of claim 1, wherein the integrated circuit is part of at least one of a hard disk drive (HDD), a solid state drive (SSD), and flash memory card.

9. The method of claim 1, wherein the step of unlocking the medical device further includes enabling a blockchain transaction.

10. The method of claim 1, wherein the step of unlocking the medical device further includes enabling a cryptocurrency transaction.

11. The method of claim 1, wherein one of the integrated circuit and the medical device has a non-fungible token (NFT) associated with it.

12. A method of unlocking an operation of a Class III medical device suitable for use in treating COVID 19 in humans, the method comprising the steps of:

inserting an integrated circuit into a medical device having a Radio Frequency Identification (RFID) reader, the medical device having a capability that is in a locked state;

the integrated circuit having a first tiny RFID tag embedded therein, the first tiny RFID tag having an area of about 0.1 mm$^2$ or less, the first tiny RFID tag being a primarily digital tag that is implemented using portable digital IP blocks, the first tiny RFID tag utilizing dual-phase RF-only logic;

wherein power supply transistors are shared across an integrated circuit chip and a foundry standard cell library is used in manufacturing the first tiny RFID tag;

reading first RFID data from the first tiny RFID tag;

verifying that the first RFID data that has been read meets criteria for unlocking the medical device; and after verifying the RFID data, unlocking the capability of the medical device for operation; wherein the medical device is a Class III medical device as defined by the Food and Drug Administration (FDA), and is suitable for use in treating COVID 19 in a human body and requires regulatory premarket approval to evaluate the safety and effectiveness of the medical device;

in which the medical device is further configured to be an internet of things (IOT) device, the method further comprising connecting the medical device to a computer network;

in which the RFID data is encoded solely at a foundry and is not user-programmable, wherein the method further comprising encoding the first tiny RFID tag with data at the foundry;

the method further comprising the step of interacting between the medical device and the integrated circuit after the RFID data is verified;

the method further comprising the step of a component interrogating the medical device, receiving a reply from the medical device, and providing the medical device access to an aspect of the component when the reply is acceptable;

wherein the integrated circuit comprises a second tiny RFID tag, the method further comprising reading data from the second tiny RFID tag;

wherein the second tiny RFID tag is imbedded in the integrated circuit, has an area of 0.1 mm$^2$ or less, and is spaced apart from the first tiny RFID tag; and wherein the method further comprises the step of verifying data from both the first and the second tiny RFID tags to unlock the medical device.

13. The method of claim 12, wherein the medical device is a transcutaneous electrical nerve stimulator and the method includes the step of performing transcutaneous electrical nerve stimulation.

14. The method of claim 12, wherein the medical device is a pulse electromagnetic field (PEMF) therapy device, and the method includes the step of performing PEMF therapy.

15. The method of claim 12, wherein the medical device has a laser, and the method includes performing laser therapy.

16. The method of claim 12, wherein the medical device may also be used in a veterinary setting on non-human animals.

* * * * *